United States Patent [19]

Smola et al.

[11] 4,004,548
[45] Jan. 25, 1977

[54] CHROMATOGRAPHIC SPOTTER

[75] Inventors: Frank M. Smola; Henri E. Breton, both of Rochester, N.Y.

[73] Assignee: Eastman Kodak Company, Rochester, N.Y.

[22] Filed: Sept. 15, 1975

[21] Appl. No.: 613,382

Related U.S. Application Data

[63] Continuation-in-part of Ser. No. 592,704, July 2, 1975, abandoned.

[52] U.S. Cl. .................................. 118/58; 23/253 R; 118/243; 118/506; 204/299 R
[51] Int. Cl.² .................................................. B05C 1/02
[58] Field of Search ............... 118/421, 76, 77, 78, 118/3, 401, 211, 58, 243, 506; 401/272, 259, 264, 265; 33/34; 346/140, 140 A, 139 C; 427/256, 445; 101/327; 204/299, 180 G; 23/253 R, 259; 73/61.1 C; 141/31, 114, 327, 392; 222/527

[56] References Cited

UNITED STATES PATENTS

| | | |
|---|---|---|
| 686,461 | 11/1901 | Keats .................................... 118/78 |
| 768,473 | 8/1904 | Manning ............................. 346/140 |
| 1,347,787 | 7/1920 | Mapelsden ......................... 346/140 |
| 1,438,829 | 12/1922 | Howell .............................. 346/139 C |
| 2,252,542 | 8/1941 | Beeh ...................................... 118/3 |
| 2,510,274 | 6/1950 | Barry et al. ......................... 118/243 |
| 3,025,830 | 3/1962 | Vierthaler et al. ................. 118/243 |
| 3,150,001 | 9/1964 | Hrdina ................................. 118/58 |
| 3,189,413 | 6/1965 | Davis ................................. 23/253 R |
| 3,199,112 | 8/1965 | Brunson et al. ............... 346/140 X |
| 3,348,235 | 10/1967 | Kawase et al. ................. 401/265 X |
| 3,780,700 | 12/1973 | La Fleur et al. .................... 118/503 |
| 3,833,341 | 9/1974 | Tocci .................................. 23/259 |

*Primary Examiner*—Morris Kaplan
*Attorney, Agent, or Firm*—D. M. Schmidt

[57] ABSTRACT

A spotting apparatus for touching a container, having a capillary exit, to a pressure-sensitive substrate, wherein the pressure of such contact does not exceed generally that provided by the weight of the container. Such pressure control is achieved by permitting relative axial movement of the exit portion of the container with respect to the activating mechanism, to compensate for overtravel of the mechanism.

13 Claims, 5 Drawing Figures

CHROMATOGRAPHIC SPOTTER

RELATED APPLICATIONS

This application is a continuation-in-part application of our copending application Ser. No. 592,704, filed July 2, 1975, now abandoned.

BACKGROUND OF THE INVENTION

1. Field of the Invention

The invention relates to apparatus for automatically spotting substrates such as thin layer chromatographic sheets. Known quantities of mixtures of chemical compounds which are to be analyzed by a comparison of their relative rates of flow through the coating under the influence of a migrating solvent are spotted on chromatographic sheets. Such sheets generally comprise a sorbent such as a silica gel, a binder such as sodium polyacrylate, and a thicker coated on a support. Because the spot enlarges upon migration, the spot initially must be very small, i.e., no larger than about 5 mm in diameter. As volumes required for such analysis generally exceed those which will form such a small spot, repeated spotting and drying of the same area of the substrate is usually necessary.

2. State of the Prior Art

Spotting of thin layer chromatographic sheets, hereinafter "TLC" sheets, by successive contacts to form a spot of proper concentration has long been done by hand. If large amounts of solution are involved, such manual labor is at best very time consuming.

Many automated approaches have been suggested to obtain the required spotting. In an attempt to mechanically duplicate the manual process of repeatedly touching a capillary tube perpendicularly to a sheet, containers have been mounted in holding bars which are brought to bear against the sheet to be spotted. Such containers have included cups, syringes, and capillary tubes, as are shown for example in U.S. Pat. Nos. 3,189,413; 3,758,275; 3,766,884; and 3,833,341 and in German DT 2,208,362. Not only have such devices been quite complex in construction, as shown in U.S. Pat. No. 3,189,413, they also have not specifically provided for the thin-skinned nature of the surface of the sheet or substrate to be spotted. That is, such sheets have coatings which are soft when wet and are easily damaged, i.e., flaked or other-wise removed, by mechanical forces indiscriminately applied by automated applicators. Such damage is particularly likely when the spotting devices are provided with sharp edges against which the sheet is moved, as in stripe lay-down, e.g., in a manner such as is disclosed in U.S. Pat. No. 3,358,496. It has been suggested that springs be used to ease the spotters into position, as is disclosed in U.S. Pat. No. 3,780,700. However, once engaged, such devices still bring to bear a large, fixed pressure incapable of change as might be necessary to accommodate a variance in sheet thickness. Such variance can be caused, for example, when sheets having different types of supports are used.

If the apparatus parts are carefully machined, when the capillary tubes are moved into contact with the substrate, they cannot be moved or pressed any farther and excessive pressure is avoided. Such close tolerances however are expensive to provide, and because of wear, are difficult to maintain.

Another approach has been to provide the test solution as a drop which falls onto the sheet rather than as a solution touched to the sheet. However, such devices, as are described, for example, in U.S. Pat. No. 3,843,053, are susceptible to wide variations in spot size, and are not suitable to the production of very small spots. Yet another approach has been to provide the capillary tubes or syringe needles with bending moment flexibility so that they can be bent to touch down into a sheet, as is shown in U.S. Pat. No. 3,738,493 and in Canadian Pat. No. 933,746. However, such devices do not place the confining walls of the capillary orifice at right angles to the sheet, as is required for minimum dispersion and maximum diffusion-to-flow ratio, or they require specially bias-cut tubes which do not provide such right angle contact.

Still another approach has been to wick the solution onto the sheet as shown, for example, in U.S. Pat. No. 3,568,634. However, residual solution may stay in the wick thereby giving rise to a false reading.

Apparatus has been constructed which provides perpendicular tube-to-sheet contact while incidentally reducing the applicator to sheet pressure. For example, in U.S. Pat. No. 3,807,959, there is disclosed apparatus comprising a plurality of sample-carrying capillary tubes clamped in a bar which in turn slides under the influence of gravity between two notched supports towards the TLC plate to be spotted. Because the bar is free to move relative to the plate being spotted, the maximum pressure applied at each capillary tube results from the weight of the bar, the tubes, and their contents. However, the massive size of the bar relative to the tubes renders this pressure of significant magnitude, and this must be reduced by tilting the support for the plate or sheet so that the sheet is nearly vertical and the bar is only slightly tilted out of the horizontal. Furthermore, such apparatus suffers the disadvantage of requiring perfect alignment of the ends of the capillary tubes in a plane parallel to the plane of the sheet, prior to clamping of the bar, as otherwise any tube which projects out of the plane will prevent the other tubes from properly contacting the sheet.

Chromatographic applicators not suitable for spot formation include hand-held devices such as shown in U.S. Pat. No. 3,495,446.

Patents directed to the background of devices for forming spots or coatings in general include U.S. Pat. Nos. 3,839,183; 3,428,547; 3,404,025; 3,317,418; 3,260,413; 2,868,020 and 2,832,140.

OBJECTS OF THE INVENTION

In view of the above-described problems of prior art constructions, it is an object of this invention to provide apparatus for repeated spotting of a substrate which minimizes the pressure applied to the substrate by the spotting mechanism without requiring expensive, precision machining of parts and tolerances.

It is a related object of the invention to provide such apparatus in a manner which will control the spot size to prevent undesired spreading.

Yet another related object of the invention is to provide such apparatus in a manner which will permit a plurality of spots to be formed simultaneously.

Other objects and advantages will become apparent upon reference to the following Summary of the Invention and Detailed Discussion, when read in light of the attached drawings.

SUMMARY OF THE INVENTION

The invention concerns a spotting apparatus, such as can be used in spotting a substrate such as a TLC sheet, which minimizes the amount of potentially damaging pressure that will be directed to the sheet or substrate. More specifically, there is provided an improved apparatus for applying a small spot of solution to a substrate, the apparatus including a container having a reservoir portion, and a tip portion provided with a capillary exit passageway fluidly connected to the reservoir portion, a mounting member having an aperture for holding the container, and means for repeatedly moving the tip portion into momentary contact with the same area of the substrate. The improvement provides at least the tip portion of the container and the member are mounted with respect to each other so as to permit substantial relative axial movement between the tip portion and the member aperture when the member is urged toward the substrate, whereby contact pressure between the container and the substrate is minimized.

DESCRIPTION OF THE PREFERRED EMBODIMENTS

The invention is particularly useful in the spotting of thin layer chromatographic (TLC) sheets, which are referred to hereinafter by way of example. However, it is not intended that it be so limited, and instead it can be applied or used whenever a solution or liquid must be spotted on a substrate which is susceptible to surface damage which can be caused by too much pressure. Thus, as used herein, "substrate" means any material having a total surface area exceeding the spotting area, which is designed to receive a small quantity of solution.

Directions such as "upwardly" and "downwardly" as used herein refer to directions the parts assume when in actual, preferred use.

The TLC sheets which are spotted by this device can be formed from a variety of layers coated upon a support such as glass or a film such as poly(ethylene terephthalate). The coating is generally on the order of from about 125 to about 250 microns thick. The nature of the coating is such as to permit the spot to be imbibed in it, rather than on it, both to control spot size and to permit solute migration under the influence of the saturating solvent. The overall thickness of the sheet will generally vary from about 275 to about 340 microns for a film support, and about 1400 to about 1700 microns for a glass support. These sheets are conventional items of commerce, so that no further details are required.

Likewise, the solutions to be spotted are conventional and depend of course upon the compound being tested. The solvents used can be selected from such exemplary liquids as acetone, benzene, chloroform, ethyl acetate, ethyl alcohol, methyl alcohol, and water.

Figure 1:
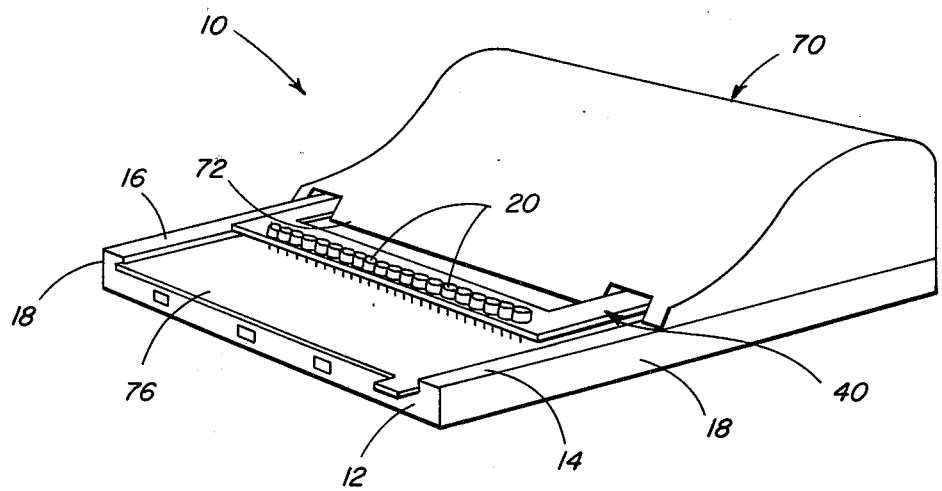
FIG. 1 is an isometric view of apparatus constructed in accordance with the invention.
Figure 2:
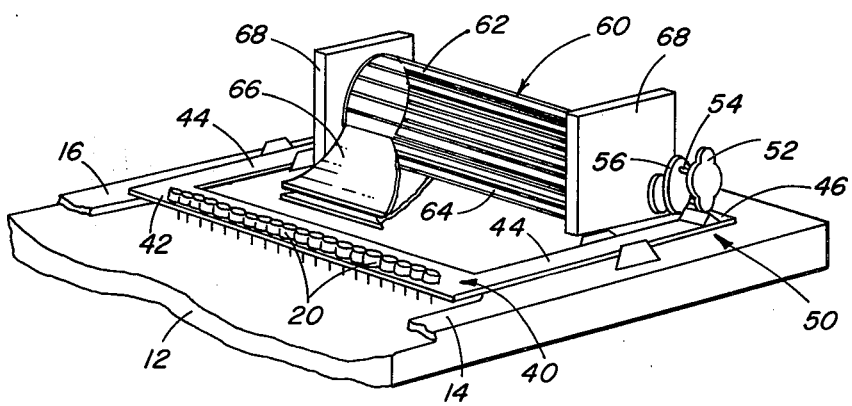
FIG. 2 is a fragmentary partially broken-away view similar to FIG. 1, illustrating the internal portions of the apparatus.

Turning now to FIGS. 1 and 2, there is illustrated a spotting apparatus 10 which comprises a base 12 which acts as means for holding the TLC sheet in a generally planar orientation, a pair of opposed shoulders 14 and 16 which rise from the base at opposite edges 18 thereof to provide a guide for the TLC sheet, a plurality of spotting containers 20 held above the base by an elongated mounting member 40, means 50 (FIG. 2) for repeatedly moving the mounting member to cause the containers 20 to contact the TLC sheets, a blower 60 for drying the spots formed by the apparatus before the next spot is deposited, and a cover 70 (FIG. 1) which is snapped into place or otherwise secured by conventional fasteners, not shown, to the base. The cover has a front portion 72 which acts as a stop to limit the forward insertion of the TLC sheet. A shim 76 can be inserted on the base between the shoulders 14 and 16 for use with film support types of TLC sheets, and is removed for sheets formed on glass supports.

Figure 4:
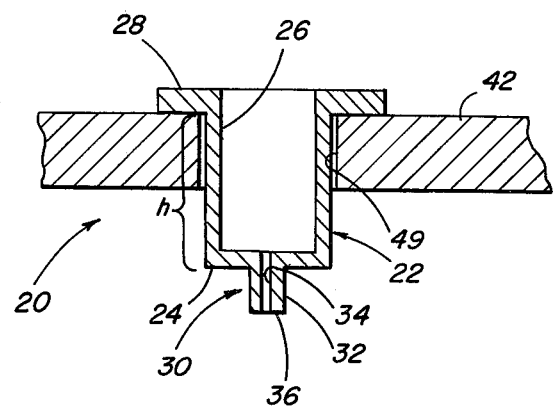
FIG. 4 is an enlarged elevational view in section illustrating the relationship between the container of the apparatus and the mounting member.

The container 20 is better illustrated in FIG. 4. It comprises a cup-like member having a reservoir portion 22 defined by a bottom wall 24 and opposed side walls 26 extending from wall 24. Preferably the side walls define a generally cylindrical shape, but other shapes can be used as well. Walls 26 preferably terminate in an annularly shaped shoulder 28 extending radially outwardly away from walls 26. A tip portion 30 is defined by opposed walls 32 extending from wall 24 in a direction away from walls 26, and is provided with a capillary exit passageway 34 which extends the full length of portion 30 to fluidly connect the reservoir portion 22 with an exterior tip surface 36. As used herein, "capillary passageway" means a bore having a diameter which is less than that which will permit gravity flow of the solutions contained therein. For most solvents used with TLC sheets, this requires a capillary passageway which will resist gravity flow for liquids having a surface tension which is no less than about 20 dynes per cm.

Still another characteristic of the capillary passageway is that the spot it forms preferably does not exceed about 5 mm in diameter. A typical bore or passageway diameter which satisfies both of these requirements is about 0.2 mm.

Preferably the portion 22 should be only large enough to accommodate solution volumes typical for TLC analysis. Thus, portion 22 should typically have a volume of from about 20 to about 50 microliters.

A great variety of material will suffice for the manufacture of container 20. Typical examples include steel, glass, and synthetic polymers such as polyethylene, the latter being particularly useful if the container is designed to be discarded after a single use to avoid the necessity of careful cleaning of containers between use.

Containers 20, FIG. 2, are freely or loosely mounted in the mounting member 40 which comprises a U-shaped bar with a mounting portion 42 and pivot arms 44 which terminate in driving ends 46. The arms 44 (FIG. 3) pivot about a pivot flange 48 attached to the base 12. To permit the container tip portion to have substantial relative axial movement which, as shown, is preferably vertical movement, with respect to the mounting portion 42, each of the containers is accommodated in an aperture 49, FIG. 4. This aperture has a generally cylindrical shape to match that of the reservoir portion 22, but an internal diameter which is substantially greater than the external diameter of portion 22 and less than the exterior dimensions of annular should 28. Thus, as used herein "substantial relative axial movement" means that which occurs when a force is applied to a container, seated in an aperture, in a direction generally aligned with the axis of the aperture, FIG. 4, the internal diameter of the aperture being substantially greater than the external diameter of the container. Thus, the relative movement between the tip portion 30 and the mounting member 40 is generally linear.

For a typical container weighing about 1.25 gms and having an external diameter of about 0.64 cm for the reservoir portion, the diameter of aperture 49 is about 0.65 cm. This provides a typical clearance of about 0.1 mm. The diameter of shoulder 28 then can be on the order of about 1.0 cm.

It will be appreciated that there is a limit to the differential which may exist between the container diameter and the aperture diameter, apart from the diameter of shoulder 28. No matter how large the latter is, this differential cannot be so large as to permit rocking of the container such that the tip portion contacts a different area of the substrate in subsequent spottings.

Figure 3:
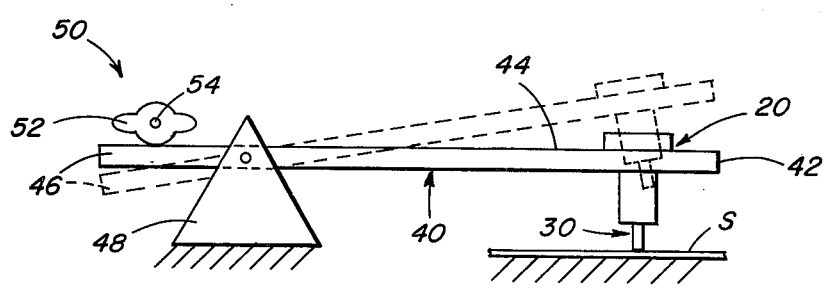
FIG. 3 is a partially schematic fragmentary view in elevation illustrating the operating principle of the apparatus.

The result is that as the mounting portion 42 pivots downwardly towards the TLC sheet, labeled S in FIG. 3, when container 20 contacts it the mounting portion is free to continue such downward motion sightly, without further increasing the pressure upon sheet S. Instead, container 20 moves upwardly relative to member 40 in the direction of arrow 47, FIG. 4, and the pressure applied to sheet S does not exceed generally that which results from the weight of the container 20 and the solution contained therein. Although the container will of course have a momentum which will add to the pressure, this is generally negligible compared to the overall weight. A typical example for a container of the type described above applies only a pressure resulting from the weight of about 1.25 gms. Yet, by virtue of the perpendicular orientation of the capillary passageway with respect to the TLC sheet, surface 36 remains flat on the sheet and spot spreading is minimized.

The amount of relative movement which exists between the container 20 and the mounting portion 42 will of course depend upon the amount of overtravel provided to the mounting member. A typical container 20 has a height $h$, FIG. 4, between the exterior surface of bottom wall 24 and shoulder 28, which permits relative movement between the tip portion 30 and portion 42 of as much as about 0.6 cm.

It will be appreciated that, preferably, each of the containers 20 is mounted in aperture 49 in the prescribed manner, so as to be movable relative to it and to each other. For ease of manufacture, the containers 20 can be substantially identical. The shape of reservoir portions 22 can be altered as long as the shape of aperture 49 is correspondingly altered and is slightly larger in dimension than the external dimensions of walls 26.

Turning now to FIGS. 2 and 3, to provide for repeated movement of tip 30 into momentary contact with the sheet S, means in the form of a prime mover 50 are provided, which can be, as shown, a multilobed cam 52 mounted on a drive shaft 54 rotated by a conventional electric motor 56 so as to press upon ends 46 of member 40. The number and positions of the lobes on the cam should be selected to achieve the desired drying time between spotting. Or alternatively, any other driving means can be used such as a solenoid controlled by a timer to raise and lower ends 46, and therefore containers 20, with respect to the TLC sheet S.

The rate at which the containers are to be contacted to, and the time during which they are in contact with, the sheet S depends of course upon (a) the size of the spot being formed, (b) the solvent used, and (c) the extent to which evaporation of the solvent is assisted by forced hot air as described hereafter. That is, contact must be limited so that the spot so formed does not exceed the desired spot size. For a capillary diameter of about 0.2 mm to form a 2 mm drop size, about 0.1 sec contact time is typical. If the rate of evaporation is assisted by forced hot air, most solvents for such a spot will evaporate in about 1 to 2 seconds, except for water which takes longer. Thus, spotting preferably is caused by means 50 to occur at the rate of about once every 2 seconds. The total time to deposit one sample will of course depend upon the solvent volume. For a volume of about 50 microliters, about 120 spottings are required. Thus, at a rate of 1 spot every 2 seconds, for 50 microliters, the entire process lasts about 4 minutes.

To assist evaporation, blower 60 can be any conventional tangential blower which draws air in, at portion 62, FIG. 2, and propels it from portion 64 preferably through an arcuate duct 66 directed to the plane in which the TLC sheet is held. A typical blower for such use is any one of the tangential blowers manufactured by Torin Corporation. The blower can be held on base 12 by suitable mounting means, such as mounting plates 68. In the event the TLC sheet tends to flutter in apparatus 10 due to the volume of air generated by blower 60, opposed guide grooves, not shown, can be mounted in shoulders 14 and 16 to hold the sheet in place.

Figure 5:
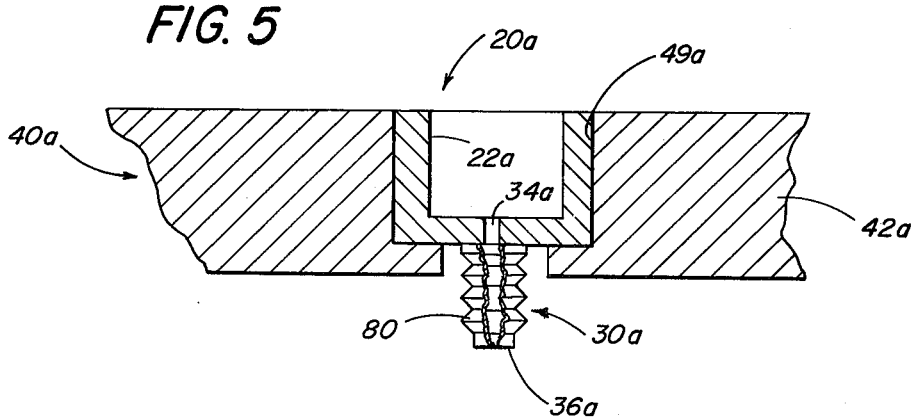
FIG. 5 is a view similar to FIG. 4 but illustrating an alternate embodiment of the invention.

Turning now to FIG. 5, there is provided an alternate form of the invention, in which just the tip portion is mounted in the mounting member for movement relative to the member. Parts similar to those previously described bear the same reference numeral to which the distinguishing suffix $a$ has been added. Thus, the mounting member 40a has a mounting portion 42a in which are provided apertures 49a to accommodate containers 20a as before, the containers comprising a reservoir portion 22a and a tip portion 30a having a capillary passageway 34a therein. Unlike the previous embodiment, the reservoir portion 22a is firmly secured in aperture 49a, as by a force-fit, screw threads, or other suitable means. Relative axial motion of tip surface 36a is achieved by providing tip portion 30a with a bellows 80 intermediate bottom wall 24a and surface 36a. By contraction, bellows 80 will permit consequent movement of the tip surface relative to portion 42a, in the direction of arrow 47a generally aligned with the aperture axis, as the latter forces the surface 36a against the TLC sheet. The pressure so generated is limited to the compression effect of the bellows, which in turn is controlled by its spring constant. By proper selection of the spring constant, the force delivered on the TLC sheet can be equal to the weight of the container and its contents or it can be reduced even below that. It will be appreciated, of course, that movement of member 40a should be limited so that it cannot be pivoted so far as to completely collapse the bellows.

The use of such a container 40a is generally as described for the previous embodiment.

The invention has been described in detail with particular reference to certain preferred embodiments thereof, but it will be understood that variations and modifications can be effected within the spirit and scope of the invention.

What is claimed is:

1. In an apparatus for simultaneously applying a plurality of small spots of solution to a substrate, the apparatus including
supporting means for supporting the substrate in a generally planar orientation, a plurality of containers each having a reservoir portion and a tip portion provided with a capillary exit passage fluidly connected to the reservoir portion,
a mounting member having a plurality of apertures, each of said containers being mounted in one of said apertures,
and means for repeatedly moving said tip portions into momentary contact with the same area of the substrate;
the improvement wherein at least the tip portion of said each container and said member are mounted with respect to each other so as to permit substantial relative axial movement between said tip portion and the member aperture when the member is urged toward the substrate and the container contacts the substrate, whereby contact pressure between said container and said substrate is minimized.

2. The improved apparatus as defined in claim 1 wherein said container is freely mounted in said aperture, said moving means lowers said tip portion into contact with a generally horizontally oriented substrate, and said relative movement is vertical, whereby the pressure of the container against the substrate is no greater than generally the weight of the container and the solution contained therein, and physical damgage to the substrate is minimized.

3. The improved apparatus as defined in claim 1 wherein said container comprises a bottom wall and opposed side walls extending therefrom to define said reservoir, said tip portion comprising opposed walls extending from said bottom wall away from said wide walls, said passageway extending the length of said tip portion into said reservoir.

4. The improved apparatus as defined in claim 3 wherein said container side walls are generally cylindrical in shape and terminate in an annularly shaped shoulder extending radially outwardly from said side walls, and wherein said elongated member has a generally cylindrical aperture therethrough, the internal diameter of said aperture being substantially greater than the external diameter of said side walls and substantially less than the external diameter of said shoulder.

5. The improved apparatus as defined in claim 1, wherein said containers are all substantially identical and are each freely mounted within said member for relative vertical movement with respect to said member and with respect to each other.

6. The improved apparatus as defined in claim 1 wherein said capillary passageway has a diameter which does not exceed that which will form a spot having a diameter of about 5 mm when said tip portion contacts the substrate and the solution diffuses into the substrate.

7. The improved apparatus as defined in claim 1 wherein said tip portion moves relative to said member when the force on the substrate exceeds about 1.25 grams.

8. In an apparatus for simultaneously applying a plurality of small spots of solution to a substrate, the apparatus including
a plurality of containers each having a reservoir portion and a tip portion provided with a capillary exit passageway fluidly connected to the reservoir portion,
a mounting member having a plurality of apertures for holding said containers,
means for holding a substrate in a generally planar orientation,
and means for repeatedly moving said tip portions perpendicularly, with respect to the substrate, into contact with the same area of the substrate, the passageway being oriented generally perpendicular to the substrate;
the improvement wherein at least the tip portion of said each container is mounted within said member to permit substantial relative axial movement between said tip portion and the member aperture when the pressure on the substrate exceeds the weight of the container and the solution contained therein, whereby physical damage to the substrate is minimized.

9. The improved apparatus as defined in claim 8 wherein said aperture has a shape corresponding to the shape of said reservoir portion and is sufficiently larger in dimension than the reservoir portion as to permit relative movement of the container held in said aperture.

10. The improved apparatus as defined in claim 8 wherein said tip portion moves relative to said member when the force on the substrate exceeds about 1.25 grams.

11. The improved apparatus as defined in claim 8, and further including a blower directed to the substrate to increase evaporation of the solvent of each spot.

12. An improved apparatus as defined in claim 8, wherein said reservoir portion is affixed to said mounting member, and further including means for moving said tip portion axially relative to said reservoir portion, whereby said tip portion but not said reservoir portion is capable of relative axial movement with respect to said member aperture.

13. An improved apparatus as defined in claim 12, wherein said tip portion includes a bellows.

* * * * *